United States Patent
Salem et al.

(10) Patent No.: US 11,071,488 B2
(45) Date of Patent: Jul. 27, 2021

(54) METHOD FOR DETERMINING THE LIKELIHOOD OF TORSADES DE POINTES BEING INDUCED

(71) Applicants: ASSISTANCE PUBLIQUE—HOPITAUX DE PARIS, Paris (FR); INSTITUT NATIONAL DE LA SANTÉ ET DE LA RECHERCHE MÉDICALE (INSERM), Paris (FR); SORBONNE UNIVERSITÉ, Paris (FR)

(72) Inventors: Joe-Elie Salem, Paris (FR); David-Alexandre Tregouet, Villiers sur Marne (FR); Jean-Sébastien Hulot, Ville d'Avray (FR); Christian Funck-Brentano, Paris (FR); Marine Germain, Montreuil (FR)

(73) Assignees: ASSISTANCE PUBLIQUE—HOPITAUX DE PARIS, Paris (FR); INSTITUT NATIONAL DE LA SANTÉ ET DE LA RECHERCHE MÉDICALE (INSERM), Paris (FR); SORBONNE UNIVERSITÉ, Paris (FR)

( * ) Notice: Subject to any disclaimer, the term of this patent is extended or adjusted under 35 U.S.C. 154(b) by 178 days.

(21) Appl. No.: 16/093,203

(22) PCT Filed: Apr. 12, 2017

(86) PCT No.: PCT/EP2017/058714
§ 371 (c)(1),
(2) Date: Oct. 12, 2018

(87) PCT Pub. No.: WO2017/178503
PCT Pub. Date: Oct. 19, 2017

(65) Prior Publication Data
US 2019/0059764 A1   Feb. 28, 2019

(30) Foreign Application Priority Data

Apr. 13, 2016  (FR) ..................................... 1653246

(51) Int. Cl.
*G16H 50/30*  (2018.01)
*A61B 5/316*  (2021.01)
(Continued)

(52) U.S. Cl.
CPC .............. *A61B 5/316* (2021.01); *A61B 5/349* (2021.01); *A61B 5/4848* (2013.01); *A61B 5/72* (2013.01);
(Continued)

(58) Field of Classification Search
CPC . A61B 5/04012; A61B 5/0452; A61B 5/4848; A61B 5/72; A61B 5/7275;
(Continued)

(56) References Cited

U.S. PATENT DOCUMENTS

| | | | | |
|---|---|---|---|---|
| 2007/0031817 A1* | 2/2007 | Yan | ..................... | G01N 33/5088 435/4 |
| 2008/0033313 A1* | 2/2008 | Couderc | ............ | A61B 5/04011 600/516 |

(Continued)

OTHER PUBLICATIONS

International Search Report and Written Opinion dated Oct. 16, 2017 for corresponding PCT Application No. PCT/EP2017/058714.

(Continued)

*Primary Examiner* — Ankit D Tejani
*Assistant Examiner* — Joshua Brendon Solomon
(74) *Attorney, Agent, or Firm* — Polsinelli PC (57) ABSTRACT

The present invention relates to the field of cardiology and, more specifically, to a novel algorithm that can be used, in particular, in a method for determining if a drug is likely to
(Continued)

induce a cardiac ventricular repolarisation disturbance, based on variations in electrocardiogram data.

18 Claims, 2 Drawing Sheets

(51) Int. Cl.
*G06K 9/00* (2006.01)
*A61B 5/00* (2006.01)
*G16H 40/63* (2018.01)
*G16C 20/30* (2019.01)
*G16H 50/20* (2018.01)
*G16H 20/10* (2018.01)
*G16H 70/40* (2018.01)
*A61B 5/349* (2021.01)
*G16H 50/00* (2018.01)

(52) U.S. Cl.
CPC ........ *A61B 5/7275* (2013.01); *G06K 9/00496* (2013.01); *G16C 20/30* (2019.02); *G16H 20/10* (2018.01); *G16H 40/63* (2018.01); *G16H 50/00* (2018.01); *G16H 50/20* (2018.01); *G16H 50/30* (2018.01); *G16H 70/40* (2018.01)

(58) Field of Classification Search
CPC ........ A61B 5/316; G16H 50/30; G16H 50/00; G16H 50/20; G16H 40/63; G16C 20/30; G06K 9/00496
See application file for complete search history.

(56) References Cited

U.S. PATENT DOCUMENTS

| | | | |
|---|---|---|---|
| 2008/0188761 A1* | 8/2008 | Couderc | A61B 5/0452 600/509 |
| 2009/0082680 A1* | 3/2009 | Totterman | A61B 5/0452 600/508 |
| 2014/0088442 A1* | 3/2014 | Soykan | A61B 5/6866 600/483 |
| 2015/0343063 A1* | 12/2015 | Helson | A61K 9/127 424/9.2 |

OTHER PUBLICATIONS

Couderc J-P. et al., "T-wave morphology abnormalities in benign, potent, and arrhythmogenic I inhibition," Heart Rhythm, vol. 8, No. 7, 2011, pp. 1036-1043.

Recanatini M. et al., "QT prolongation through hERG K+ channel blockade: Current knowledge and strategies for the early prediction during drug development," Medicinal Research Reviews, vol. 25, No. 2, 2005, pp. 133-166.

Clark M. et al., "Fragment-Based Prediction of the Clinical Occurrence of Long QT Syndrome and Torsade de Pointes," Journal of Chemical Information and Modeling, vol. 49, No. 11, 2009, pp. 2617-2626.

Bottino D. et al., "Preclinical cardiac safety assessment of pharmaceutical compounds using an integrated systems-based computer model of the heart," Progress in Biophysics and Molecular Biology, vol. 90, No. 1-3, 2006, pp. 414-443.

Suzuki S. et al., "In silico risk assessment for drug-induction of cardiac arrhythmia," Progress in Biophysics and Molecular Biology, vol. 98, No. 1, 2008, pp. 52-60.

Garnett C., "FDA's Model-Based Strategies in the ICH E14 Gidelines," The 12th Kitasato University—Harvard School of Public Health Symposium, 2013, pp. 1-20.

Graff C. et al., "Covariate Analysis of QTc and T-Wave Morphology: New Possibilities in the Evaluation of Drugs That Affect Cardiac Repolarization," Articles-Nature Publishing Group, vol. 88, No. 1, 2010, pp. 88-94.

Sekarski N. et al., "Medicaments et QT long," Pediatrica, vol. 19, No. 4, 2008, pp. 31-36.

* cited by examiner

METHOD FOR DETERMINING THE LIKELIHOOD OF TORSADES DE POINTES BEING INDUCED

CROSS-REFERENCE TO RELATED APPLICATIONS

This application is a national stage application (under 35 U.S.C. § 371) of PCT/EP2017/058714, filed Apr. 12, 2017, which claims benefit of French Application No. 1653246, filed Apr. 13, 2016, which are incorporated herein by reference in their entireties.

TECHNICAL FIELD

The present invention relates to the cardiology field, and more particularly to a novel algorithm that can be used in particular in a method for determining whether a drug is capable of inducing cardiac ventricular repolarization disorders, associated or not associated with a ventricular rhythm disorder of Torsades de Pointes type.

PRIOR ART

Torsades de pointes refers to a particular type of ventricular tachycardia, that is to say a cardiac ventricle rhythm disorder, resulting in accelerations of heart rate such as tachycardia (nevertheless different than ventricular fibrillation).

There are two types of torsades de pointes: torsades de pointes with long QT interval and polymorphic ventricular tachycardia with normal intercritical QT with twisted appearance.

Drug-induced torsades de pointes are a public health problem on the individual scale and on the societal scale. In the vast majority of cases, the mechanism of action of this adverse effect is the inhibition of a potassium channel involved in ventricular repolarization, called IKr, which induces a prolongation of the repolarization phase and electrocardiographically results in particular in a prolonging of the QT interval corrected with respect to heart rate (QTc).

As mentioned, in Sekarski et al. (Paediatrica, vol. 19, No. 4, 2008), the prolonging of the QT interval can cause a ventricular arrhythmia that can degenerate and result in sudden death. The prolonging of QT thus currently constitutes one of the most frequent causes of restriction of use and of withdrawal of drugs from the market. Among the drugs thus withdrawn from the market, this publication cites in particular cisapride, terfenadine, droperidol or sertindole.

These phenomena are particularly observed with class III anti-arrhythmics, which as a priority block potassium channels, thus prolonging repolarization. The class III anti-arrhythmics currently on the market all have a basic structure which includes a methanesulfoaniline group (or a bioisostere thereof). Mention may thus be made of amiodarone (Cordarone®), azimilide, bretylium, clofilium, dofetilide, ibutilide (Corvert®), sematilide, sotalol (Sotalex®) and dronedarone (Multaq®).

The above publication presents, in tables 1 and 2, a certain number of drugs known to prolong QT. This publication also recalls that the "University of Arizona Center for Education and Research on Therapeutics" has established and maintains a database of these drugs that can be found on their website www.torsades.org or https://crediblemeds.org/.

In the process for the filing of a file for a marketing authorization for a new drug, all the molecules must have an evaluation of their torsadogenic potential (potential for inducing a torsade de pointes). This evaluation involves, in human beings, thorough studies of the modifications, induced by the new drugs, of ventricular repolarization and particularly of prolongation of the QT interval, or of corrected prolongation QTc. This prolongation of the QTc interval is the marker currently recommended for estimating the degree of IKr inhibition of a drug administered to subjects with normal ventricular repolarization in the basal state.

Thus, it is considered that a test molecule is at significant risk justifying a close monitoring of this rhythmic risk during placing on the market when the increase in QTc is greater than 20 ms. When the QT/QTc prolongation is between 5 and 20 ms, this situation is in a "gray area" and additional studies must be carried out in order to lead to a more reliable conclusion. It is generally considered that a molecule is safe with regard to cardiac repolarization when a QT/QTc prolongation of less than 5 ms is observed.

However, the prolongation of this QTc interval is a very imperfect parameter, which is not very specific for ventricular IKr channel inhibition. Thus, if an inhibition of the IKr channel increases the QT interval, the latter can be increased without IKr inhibition, the risk of drug-induced torsade de pointes then being less great. Some useful molecules will then have their development interrupted because of an overestimation of this risk when other molecules will have their development continued despite an underestimated torsadogenic risk.

On the individual scale, drug-induced torsades de pointes can affect subjects without great comorbidity and can result in death. The determinants of this individual risk are still poorly understood, with in particular an increased risk identified in the case of hypokalemia, and of congenital long QT, but there is no reliable diagnostic test for evaluating this personal risk, especially in the event of normal QTc interval in the basal state.

Thus, both the regulatory authorities (such as the Food and Drug Administration) and clinicians-physicians are seeking new more relevant methods for predicting the torsadogenic risk of drugs, in the pre-marketing evaluation, or for a particular patient, which go beyond simple analysis of the increase in QTc interval duration after pharmacological stress.

Sotalol is an anti-arrhythmic drug recommended and used for controlling rhythm in patients with atrial fibrillation. Sotalol has a high capacity to block the IKr potassium channel, associated with a dose-dependent risk of induction of torsades de pointes, reaching up to 7% of patients treated. Sotalol has linear pharmacokinetics, a virtually complete absorption without great variability, and a maximum concentration observed 3 to 5 hours after oral intake.

Couderc et al. (Heart Rhythm. 2011 July; 8(7):1036-43) describe the analysis of traces and of QTc, TAmp or TpTe values at various times, but do not deal with the dynamics of the parameters after treatment; thus, this document does not calculate the ΔQTc, ΔTAmp and ΔTpTe values as envisioned in the present application, nor does it calculate a principal component on the basis of these values.

US 2008/188761 describes a method for detecting potassium channel delays by comparison of the correlation between the TAmps and the heart rate, but does not describe to any greater extent the ΔQTc, ΔTAmp and ΔTpTe values as envisioned in the present application, or calculate a principal component on the basis of these values.

Recanatini et al. (Med Res Rev. 2005 March; 25(2):133-66) describe, in a review article, the link between QT prolongation and torsades de pointes, but do not mention or suggest the strategy envisioned in the present application.

Clark et al. (J Chem Inf Model. 2009 November; 49(11): 2617-26) describe a method for determining the association between long QT and torsades de pointes for various molecules, but do not mention or suggest the strategy envisioned in the present application.

Bottino et al. (Prog Biophys Mol Biol. 2006 January-April; 90(1-3):414-43) describe a method that can be used for analyzing whether certain drugs are capable of inducing torsades de pointes, but do not mention or suggest the strategy envisioned in the present application.

Suzuki et al. (Prog Biophys Mol Biol. 2008 September; 98(1):52-60) describe in silico methods for determining whether a molecule is capable of inducing a cardiac arrhythmia, but do not mention or suggest the strategy envisioned in the present application.

There is therefore a need to set up a test which makes it possible to predict the risk that a drug can induce a torsade de pointes, after administration in patients.

Alternatively, it is also advantageous to determine whether a particular patient has a specific risk of presenting a torsade de pointes, after administration of a specific drug.

SUMMARY OF THE INVENTION

The invention proposes to provide a method for easily determining, after a simple electrocardiogram measurement, whether a patient is likely to present a torsade de pointes event after administration of a drug.

The inventors have thus demonstrated the fact that it is possible to obtain a reliable quantitative result of the capacity for a substance to inhibit the IKr potassium channel (general effect of the substance) or for a patient to present such an inhibition of the IKr potassium channel after administration of a substance capable of inhibiting it (patient's individual response effect), by studying not only the QTc, but two additional values, the maximum amplitude of the T wave (TAmp) and the duration between the peak and the end of the T wave (TpTe).

By combining the variations observed between the three values mentioned above, the inventors have defined an algorithm which makes it possible to provide a precise piece of information as to the risk of occurrence of a cardiac repolarization disorder induced by a substance.

The algorithm proposed by the inventors is particularly advantageous in that it makes it possible both to obtain information on a particular substance or composition, when tested on a cohort of patients, and also to determine the individual risk for a particular patient, which makes it possible to perform appropriate monitoring of the patients at risk, while decreasing the cost of monitoring the patients who are a priori not at risk.

Measurements Used in the Context of the Invention

The following measurements are thus used:

TAmp: Maximum Amplitude of the First Peak of the T Wave

The difference (expressed as percentage) between the maximum amplitude of the first peak of the T wave before and after administration of the substance that it is desired to test is calculated. In fact, in the event of "notch", it is possible to observe two peaks of the T wave. The amplitude of the first peak should be measured even if it is less than the second.

The datum calculated is thereof $\Delta$TAmp (%)=((TAmp before administration—TAmp after administration)/(TAmp before administration))×100

The difference between the amplitude of the T wave before administration and that after administration is in this case calculated so that $\Delta$TAmp is positive. This is due to the fact that the inhibition of the IKr channel induces a decrease in the amplitude of the T wave. The performing of the above calculation makes it possible to reflect this decrease as a percentage. The expression of the results in absolute values (mV) also makes it possible to calculate an operating algorithm.

The difference between the amplitude of the T wave after administration and that measured before administration could however have been calculated, and $\Delta$TAmp would have been negative.

The TAmp value that is taken into consideration in this formula is preferentially an average of several TAmp measurements.

The measurements can be carried out on the derivations (leads) that a practitioner will choose, but preferentially on the D2, V2, V3 derivations. These measurements can also be performed on the V4 or V5 leads, in particular if TAmp before administration of the substance is less than 0.1 mV.

In one particular embodiment, and in order to decrease the potential errors due to the variations that may exist in the patient during the ECG measurement, it is preferred to measure the TAmp value on an averaged complex (generally generated by a standard median complex (template) obtained from the recordings made during 10 seconds), or even on the average of three averaged complexes generated a few minutes apart.

TpTe Interval Between the Maximum First Peak of the T Wave and the End of the T Wave (TpTe)

The difference (expressed as a percentage) between the maximum first peak of the T wave and the end of the T wave, before and after administration of the substance that it is desired to test, is calculated.

The datum calculated is therefore $\Delta$TpTe (%)=((TpTe after administration—TpTe before administration)/(TpTe before administration))×100

The TpTe value that is taken into consideration in this formula is preferentially an average of several TpTe measurements.

The measurements can be carried out on the leads that a practitioner will choose, but preferentially on the V2, V3, V4 leads. The measurements can also be carried out on the V5 or V6 leads.

In one particular embodiment, and in order to decrease the potential errors due to the variations that may exist in the patient during the ECG measurement, it is preferred to measure the TpTe value on an averaged complex (generally generated by a standard median complex (template) obtained from the recordings made for 10 seconds), or even on the average of three averaged complexes generated a few minutes apart.

The absolute value (in msec) of the TpTe variation can also be used in the context of the algorithm.

QTcF QT Interval Corrected With Respect to the Heart Rate

QTc

The difference (expressed as a percentage) between the QT interval corrected with respect to heart rate is calculated using a suitable method which minimizes the influence of the heart rate on the QTc value, that is to say establishes a slope not different than zero in the relationship QTc as a function of heart rate (usually, in adults, the appropriate correction is carried out by the method of Fridericia, QTcF), before and after administration of the substance that it is desired to test.

It is recalled that $$QTcF = \frac{QT}{\sqrt[3]{RR}}$$

RR being the interval between the beginning of a QRS complex and the beginning of the next QRS complex expressed in seconds.

The datum calculated, for the use of QTcF, is therefore

ΔQTcF (%)=((QTcF after administration−QTcF before administration)/(QTcF before administration))×100

The QTcF value that is taken into consideration in this formula is preferentially an average of several QTcF measurements, in particular an average of at least three consecutive complexes. As with the other values seen above, use may be made of the QTcF value that is obtained on a median complex obtained from a recording of a few seconds, or an average of averaged complexes.

The measurements can be carried out on the leads that will be chosen by a practitioner, but preferentially on the D2 lead.

However, QTc could also be calculated by any method known in the art, in particular the method of Bazett (QTcB):

$$QTcB = \frac{QT}{\sqrt{RR}}$$

Here again, it is possible to use the absolute value of ΔQTc, rather than the percentage variation.

In general, it is preferred to calculate ΔTAmp, ΔQTc and ΔTpTe such that they all have the same sign.

Algorithm to be Implemented in the Context of the Invention

The algorithm proposed below makes it possible to obtain a quantitative value, called PC1, which is very well associated with the appearance of ECG sign determining an IKr inhibition, and presumed to be associated with an increased risk of episode of torsade de pointes with long QT.

PC1=a1×ΔTAmp (%)+a2×ΔQTcF (%)+ a3×ΔTpTe (%)+b in which
−0.05≤a1≤−0.030
−0.2≤a2≤−0.1
−0.04≤a3≤−0.02
1.5≤b≤2.
Preferably,
−0.040≤a1≤−0.035
−0.16≤a2≤−0.145
−0.35≤a3≤−0.025
1.7≤b≤1.9.
In one preferred embodiment,
a1=−0.038±0.002
a2=−0.15±0.001
a3=−0.031±0.002
b=1.79±0.05.
In one preferred embodiment,
a1=−0.03814
a2=−0.15074
a3=−0.03059
b=1.79249.

In one particular embodiment,

PC1=−0.038×ΔTAmp (%)−0.151×ΔQTcF (%)− 0.0306×ΔTpTe (%)+1.792

The more negative the PC1 value is, the more the substance administered inhibits the IKr channel and the more the patient is presumed to present a risk of having an episode of torsade de pointes.

These algorithms and values are valid when ΔTAmp is calculated as indicated above for it to be positive. If ΔTAmp is calculated such that it is negative, the values of the algorithm will change, and a new algorithm may be defined using the method described below. Likewise, if the absolute values of the differences between TAmp, TpTe and QTc are used, an algorithm having other values will be obtained.

Evaluation of a Torsadogenic Potential of a Drug

As seen above, it is important to be able to evaluate the torsadogenic potential of a compound, during clinical trials prior to the obtaining of a marketing authorization, in order to be able to draft the possible precautions for use of this drug.

The torsadogenic potential of a substance is the potential of this substance to induce a torsade de pointes after administration in a patient.

The FDA (Food and Drug Administration) and the EMA (European Medicines Agency) have published guidelines resulting from the International Conference for Harmonization (ICH) on how to carry out these trials, under the title *E14 Clinical Evaluation of QT/QTc Interval Prolongation and Proarrhythmic Potential for Non-Antiarrhythmic Drugs.*

These guidelines are accessible on the website of this agency, and are accompanied by questions and answers.

The address of the guidelines is: fda.gov/downloads/drugs/guidancecomplianceregulatoryinformation/guidances/ucm073153.pdf The capacity of non-antiarrhythmic drugs or substances to prolong cardiac repolarization can be measured by the prolongation of the QT interval on the surface electrocardiogram (ECG). It is recalled that this QT interval represents the duration of the depolarization and the subsequent ventricular repolarization and is measured from the beginning of the QRS complex to the end of the T wave. A cardiac repolarization delay creates an environment which promotes the development of cardiac arrhythmias, mostly clearly a torsade de pointes (TdP), but possibly other ventricular tachyarrhythmias also.

As seen above, the QT interval is an imperfect biomarker for the risk of proarrhythmic effect, but there is, in the general population, a qualitative relationship between QT interval and the risk of torsade de pointes, especially for drugs which cause a substantial prolongation of QT interval.

In general, the value of the QT interval measured is corrected (obtaining of QTc) so as to take into account the heart rate, this QT interval having an inverse relationship with said heart rate. However, it is not clear whether the development of the arrhythmia is more closely linked to an increase in the QT interval, absolutely, or in the QTc.

Most of the drugs which have a risk of inducing torsade de pointes increase the absolute QT interval and the QTc.

In general, when the test molecule increases the QTc by a period of less than 5 ms, it is considered that said molecule is safe in this regard. When it increases the QTc by a period of 20 ms, the effects of the molecule will have to be the subject of post-marketing monitoring. When the molecule increases QTc by a period of between 5 ms and 20 ms, this is a "gray area", that is to say that it is not possible to conclude, a priori, as to the actual risk of torsade de pointes, and that additional analyses and studies are required.

It is therefore required to rigorously characterize the effects of new drugs with regard to the risk of delaying cardiac repolarization. The algorithm defined above makes it possible, in particular if the studies are carried out with sotalol at 80 mg as positive control, to provide valuable additional information in the gray area of increase in QT/QTc of between 5 and 20 ms.

At this stage, the study is carried out on a cohort of patients. Carrying out these studies on a sufficient number of patients thus makes it possible to obtain results which present a statistical reality for the molecule that it is desired to test (drug of interest), eliminating the inter-patient variations.

A placebo and the substance of interest will preferentially be compared in order to determine whether this substance prolongs QT interval (the intervals could be measured without using a placebo, but it is preferable to use a placebo in order to take into account the natural change in the QT over the course of the day).

Advantageously, positive controls for the prolongation of QT interval will also be used. Thus, in the FDA guidelines, the former recommends the use of a positive control which increases QT/QTc by approximately 5 ms, in order to verify that this low-amplitude effect is clearly detected. Two positive controls can be used, one increasing QT interval by inducing clear inhibition of the IKr potassium channel (such as sotalol), and another control increasing QT interval without significant inhibition of the IKr channel, such as oral moxifloxacin. Any drug known to prolong QT can be used as a control, in particular as cited in tables 1 or 2 of Sekarski et al.

However, because of the potential risks posed by these drugs of tables 1 and 2 of Sekarski et al., sotalol at 80 mg is preferably used as positive control. This molecule, at this concentration, has many advantages:

the maximum concentration is well known (approximately three hours after oral administration), which makes it possible to easily plan the moment at which to take the measurements measured above.

This molecule is known to inhibit the IKr channel.

This molecule, at this concentration, increases QT/QTc by approximately 20 ms.

This molecule, at this concentration, does not induce an episode of torsade de pointes, and is therefore safe for the patient. It is however known that this molecule, at its clinical used doses (used up to 320 mg), can induce torsades de pointes.

The study is carried out on a cohort of patients, according to a protocol which may be the following, for each patient:

The TAmp, TpTe and QTc are measured on the patient before administering the substance of which it is desired to study the torsadogenic potential.

The same parameters TAmp, TpTe and QTc are measured on the patient after administration of the substance (which may thus be the placebo, the substance of interest or the positive control).

A single measurement of these parameters may be carried out (if, for the substance, the pharmacokinetics and the concentration peak of the substance in the patient's blood stream are known), but several measurements are preferably carried out at several time intervals (for example every ¼ hour or every hour, depending on the half-life of the molecule).

Periodically revealing the TAmp, TpTe and QTc makes it possible to enhance the possibility of detecting the potential torsadogenic effect of the substance, or even of determining at what moment this effect is greatest.

The ΔTAmp, ΔTpTe and ΔQTc values are calculated according to the formulae indicated above.

The algorithm mentioned above is used in order to calculate the result for each substance tested.

In general, those skilled in the art will be capable of defining the appropriate protocol as a function of the substance of interest (times at which the TAmp, TpTe and QTc will be measured), taking into account in particular the FDA guidelines as mentioned above. In particular, if sotalol is used as positive control (inhibition of the IKr channel), the above values are measured three hours after administration, which corresponds to the most frequent concentration peak of this substance. If another substance is used as control, the most appropriate time, corresponding to that at which the effect on the depolarization is the greatest, is chosen to measure the above values. Since these controls are known, those skilled in the art thus know how to determine these times. Likewise, the optimal concentrations of the controls used will be determined by those skilled in the art as a function of their knowledge of the control molecules that they will use. Thus, they may use sotalol at the dose of 80 mg for the reasons of rhythmic risk set out above. The use of a greater amount of sotalol could optionally be envisioned, but it is not however preferred because of the risks to the patient and because of its non-conformity to the recommendations for initiation of the treatment in patients who have an indication thereof.

In the definition of the protocol by those skilled in the art, it is preferred to carry out the various measurements at the same time of the menstrual cycle, when the patient is female. This is because it is known that the level of hormones influences the risk, in a woman, of repolarization disorders (long QT).

In general, as indicated above, the above steps are carried out for each patient of a cohort of patients, and a value calculated by the algorithm described above is thus obtained for each patient (and for each time at which the TAmp, TpTe and QTc parameters are measured), and for each substance.

For each time at which the TAmp, TpTe and QTc parameters were measured, it is preferred to average the values obtained for each patient, and for each substance administered (substance of interest and optionally the placebos and positive control(s)). This makes it possible to dispense with "the patient effect", that is to say the fact that two patients are capable of reacting differently to a drug or a given substance.

The value of the average of the PC1 values is then a value which takes more account of the actual presumed torsadogenic effect of the substance of interest.

It is preferable for the cohort of patients (the number of patients on which the substance of interest is tested) to be at least 10 patients, preferably at least 20 or even 50 or 100 patients. Those skilled in the art will be capable of determining the minimum number of subjects in the cohort of patients in order to obtain results which are statistically significant.

Likewise, before carrying out these studies, it is preferable for those skilled in the art to have carried out pharmacokinetic studies and dose-response studies on the substance of interest, in order to determine the best times to measure the three physiological values mentioned above.

In order to determine the torsadogenic potential of the substance of interest, the analysis will be different depending on whether or not controls are used.

If Sotalol is Used as Positive Control for Inhibition of the IKr Channel

The PC1 value is calculated for each patient, for the placebo, sotalol three hours after administration, and the substance of interest (test molecule), at the times determined by the practitioner, as a function of the pharmacokinetic characteristics of the test molecule.

An average of these PC1 values is then calculated for each of the molecules (test, sotalol, placebo), along with the median.

If the average, or alternatively the median, of PC1 for the test-molecule group is significantly lower than that obtained for the sotalol group, this test molecule thus induces an inhibition of the IKr channel beyond a risk judged to be reasonable and will have to be the subject of additional tests and of increased monitoring after it is placed on the market.

If the average of PC1 for the test-molecule group is not significantly different to that obtained for the placebo, then the molecule can be considered as not being at risk.

If the average of PC1 for the test-molecule group is significantly less than that calculated for the placebo, but is not significantly different than the average of PC1 for sotalol, this is then a "gray area". A torsadogenic risk exists since it exists with sotalol, potentially, at least, at higher doses.

Monitoring of use will then have to be set up if an increase in QT/QTc of greater than 5 ms was observed for the test molecule compared with the placebo.

The analysis is equivalent if a positive control other than sotalol was used, this being one that must however induce an increase in QT and an inhibition of the IKr channel with a torsadogenic risk considered to be more or less equivalent to that associated with 80 mg of sotalol.

If a Positive Control has not been Used

The algorithm defined above can also be used in the absence of positive control, even though not using a positive control is not recommended.

In this case, it is preferable for the population in which the trials are carried out to contain approximately 50% women and 50% men, although it is possible to go up to 60% women and 40% men (or 40% women and 60% men), according to the FDA guidelines. The patients are generally from 18 to 60 years old.

Because of the greater risk, for women, of developing repolarization disorders compared with men, the use of a cohort of patients having the above distribution makes it possible to increase the relevance of the result of the algorithm and the confidence that can be taken from the results obtained, and the analysis that can be made with said results.

The PC1 value is calculated for each patient, for the placebo, and the substance of interest (test molecule), at the times determined by the practitioner, depending on the pharmacokinetic characteristics of the test molecule.

If the average of PC1 for the test-molecule group is not significantly different than that obtained for the placebo, then the molecule can be considered as not being at risk.

If the average of PC1 for the test-molecule group is significantly greater than that obtained for the placebo, then the molecule can be considered as not being at risk.

If the average of PC1 for the test-molecule group is negative, and significantly less than that obtained for the placebo group, this test molecule is at risk and will have to be the subject of additional tests and of increased monitoring after it is placed on the market.

If the average of PC1 for the test-molecule group is negative, and not significantly less than that calculated for the placebo, this is then a "gray area". Use monitoring will then have to be set up if an increase in QT/QTc of greater than 5 ms was observed for the test molecule compared with the placebo.

In the event of torsadogenic potential determined by the method described above or if the molecule is in the gray area, more thorough studies will be carried out in order to confirm this potential and to qualify it and quantify it to a greater extent.

In the absence of positive control, it is preferable to carry out the studies on a number of patients sufficient to perform the appropriate statistical analyses.

Evaluation of a Patient's Individual Risk of Experiencing a Torsade De Pointes Event The algorithm described above also makes it possible to evaluate a patient's individual risk of experiencing a torsade de pointes event, after administration of a substance which has a torsadogenic potential.

To do this, the following protocol can be followed:

The TAmp, TpTe and QTcF are measured on the patient before administering sotalol.

The same TAmp, TpTe and QTcF parameters are measured on the patient, three hours after administration of sotalol. As seen above, it is known that sotalol has a maximum concentration approximately 3 hours after having been taken orally, and a single dose of 80 mg is preferably used.

The $\Delta$TAmp, $\Delta$TpTe and $\Delta$QTcF values are calculated according to the formulae indicated above.

The algorithm above is applied to these values, in order to obtain a final PC1 result.

The analysis of the results is carried out in the following way:

If $PC1 \leq -3.2$: a very high risk of experiencing a torsade de pointes event (this value corresponds to the 5th percentile in women who are more at risk than men, that is to say that only 5% of women have a PC1 below this value).

If $-3.2 < PC1 \leq -2.4$: the patient has a risk that is high, but slightly lower (between the 5th and 10th percentile of women).

If $-2.4 < PC1 \leq -1.25$: the patient has an average risk (corresponding to the decile-quartile in women).

If $-1.25 < PC1 \leq -0.48$: the patient has a low risk, corresponding to the quartile-45th percentile for women and to the 5th percentile for men.

If $-0.48 < PC1 \leq -0.22$: the patient's risk is very low, this range corresponding to the 45th-53rd percentile for women and to the 5th-10th percentile for men.

If $PC1 > -0.22$, the patient can be considered as having no risk.

Preferably, a small amount of sotalol is used, that is to say equivalent to the amount generally administered at the start of the clinical treatment. Thus, it is preferred for the dose of sotalol administered to the patient to be 80 mg (single oral intake), which makes it possible to observe a repolarization disorder without endangering the patient. This is because it is known that sotalol can inhibit the IKr potassium channel. The algorithms described above were validated on cohorts of patients having received a single dose of 80 mg of sotalol, the measurements having been carried out three hours after administration. The values obtained are reliable quantitative values which correlate with inhibition of the IKr potassium channel.

Thus, the result of the algorithm makes it possible to indicate whether or not the patient is likely to react to a drug which has the capacity to inhibit the IKr channel. This test is therefore more informative than the simple measurement of QT/QTc.

Depending on the result obtained and the risk thus determined for the patient, those skilled in the art will be capable of adjusting the required monitoring of the patient.

The invention therefore relates to a novel tool for generating a quantitative variable of inhibition of the IKr potassium channel.

The invention thus relates to an ex vivo or in vitro method for determining the risk of induction of a torsadogenic effect after administration of a composition in a patient, comprising the following steps:
I. combining, in an algorithm, obtained by the following method:
   a. bringing together a cohort containing a number n of patients, n being greater than or equal to 50, 75, or even 100;
   b. administering thereto an IKr-channel-inhibiting drug;
   c. measuring the QTc, TAmp and TpTe before and after administration of this drug with
      i. QTc=QT interval corrected with respect to heart rate;
      ii. TAmp=maximum amplitude of the first peak of the T wave;
      iii. TpTe=interval between the maximum first peak of the T wave and the end of the T wave;
   d. calculating the $\Delta$QTc, $\Delta$TAmp and $\Delta$TpTe corresponding to the variation, as percentage, of the QTc, TAmp and TpTe values obtained after administration of the drug, compared with those measured before administration for each of the patients;
   e. carrying out a principal component analysis on the $\Delta$QTc, $\Delta$TAmp and $\Delta$TpTe values in order to generate three new quantitative variables PC1, PC2 and PC3;
   f. said algorithm being the formula which makes it possible to obtain the PC1 variable from the $\Delta$QTc, $\Delta$TAmp and $\Delta$TpTe;
II. obtaining a final result of this combination;
III. comparing the value of this final result to a reference value.

In another embodiment, the $\Delta$QTc, $\Delta$TAmp and $\Delta$TpTe used in I.d are the absolute values of the differences, and not the percentage variations.

In this embodiment, the method is in vitro or ex vivo, that is to say that it is not applied to the human body. It uses data which were recorded by electrocardiogram on a patient, but does not comprise these steps of collecting the data. This method is not therefore applied to the human body.

The application also describes a method for determining the risk of induction of a torsadogenic effect after administration of a composition in a patient, comprising the following steps:
I. measuring, in the patient, the QTc (QT interval corrected with respect to heart rate), TAmp (maximum amplitude of the first peak of the T wave) and TpTe (interval between the maximum first peak of the T wave and the end of the T wave) values before and after administration of this composition;
II. calculating the $\Delta$QTC, $\Delta$TAmp and $\Delta$TpTe values corresponding respectively to the difference, as a percentage, of these measurements obtained after and before administration;
III. combining, in an algorithm, obtained by the following method:
   a. bringing together a cohort containing a number n of patients, n being greater than or equal to 50, 75 or 100;
   b. administering thereto an IKr-channel-inhibiting drug;
   c. measuring the QTc, TAmp and TpTe before and after administration of this drug;
   d. calculating the $\Delta$QTc, $\Delta$TAmp and $\Delta$TpTe corresponding to the variation, as a percentage, of the QTc, TAmp and TpTe values obtained after administration of the drug, compared with those measured before administration for each of the patients;
   e. carrying out a principal component analysis on the $\Delta$QTc, $\Delta$TAmp and $\Delta$TpTe values in order to generate three new quantitative variables PC1, PC2 and PC3;
   f. said algorithm being the formula which makes it possible to obtain the PC1 variable from the $\Delta$QTc, $\Delta$TAmp and $\Delta$TpTe;
IV. obtaining a final result of this combination in the algorithm;
V. comparing the value of this final result to a reference value.

This method may also be an embodiment of the invention.

In another embodiment, the $\Delta$QTc, $\Delta$TAmp and $\Delta$TpTe used in II and III.d are the absolute values of the differences, and not the percentage variations.

The methods thus described also make it possible to determine whether the composition used inhibits the IKr potassium channel in a patient, the final result obtained after application of the algorithm being quantitatively linked to inhibition of the IKr channel.

The algorithm used in the methods above is that described above. Example 1 describes how a particular algorithm was obtained.

In general, in order to obtain an algorithm that can be used in the context of the methods described in the present application, the process below is followed:
a. bringing together a cohort containing a number n of patients. Preferably, the number n of patients monitored is greater than or equal to 50, 75 or even 100, in order to obtain results which have an actual statistical value; preferably, the cohort contains an equal number of women and men or no more than 60% women and 40% men or vice versa. This makes it possible to obtain an algorithm that can be used regardless of the sex of the patient. However, this method for obtaining an algorithm can also be carried out using a population of exclusively female or exclusively male patients. The algorithms obtained will then be different, because of the greater inhibition of the IKr channel observed in women compared with men. In the context of the methods according to the invention, one or other algorithm will then be used depending on the sex of the patient on which it is desired to carry out the study;
b. administering to each patient a drug which prolongs QT, preferably by inhibiting the IKr channel.
   The drug that is administered at this step is a drug as described above, in particular the products of tables 1 or 2 of Sekarski et al. This drug is chosen by those skilled in the art as a function of its pharmacokinetic characteristics, and the doses are adjusted in order in particular not to endanger the patients of the cohort, while at the same time allowing the observation of the prolongation of QT linked to this drug in a sufficient number (sufficient for statistical analysis) of patients.

It is thus preferred to use sotalol, in particular at 80 mg orally, for the reasons mentioned above;

c. measuring the QTc, TAmp, TpTe before and after administration of this drug.

These values are measured before the administration of the drug in step b) (the measurement before this administration thus possibly being described as step b0), and after this administration. Because the drug used in step b is known to those skilled in the art, the measurement after administration is carried out at an optimum time, determined by those skilled in the art as a function of the pharmacokinetic properties of the drug of step b), such that the prolongation of QT induced by this drug is maximal. This corresponds in general to the time at which the plasma concentration of the drug is maximal. If sotalol is chosen as drug in step b), the measurements are carried out 3 hours after administration;

d. calculating the ΔQTc, ΔTAmp and ΔTpTe corresponding to the variation, as a percentage, between the QTc, TAmp and TpTe values obtained after administration of the drug, compared with those measured before administration, for each of the patients.

The ΔQTc, ΔTAmp and ΔTpTe values are thus preferentially calculated according to the formulae indicated above. ΔTAmp could however be calculated according to the formula ΔTAmp=((TAmp after administration−TAmp before administration)/(TAmp before administration)×100.

In another embodiment, the ΔQTc, ΔTAmp and ΔTpTe calculated are the absolute values of the differences, and not the percentage variations;

e. carrying out a principal component analysis on the ΔQTc, ΔTAmp and ΔTpTe values in order to generate three new quantitative variables PC1, PC2 and PC3.

Principal component analysis (PCA) is a method for converting correlated variables into new variables that are decorrelated from one another.

In one particular embodiment, a PCA is carried out in order to convert the three variables ΔQTc, ΔTAmp and ΔTpTe into three new decorrelated variables PC1, PC2 and PC3.

PCA analysis is a method known in the art, which can be carried out in particular using any software known in the art.

The algorithm that can be used in the methods described above is the formula which makes it possible to obtain the PC1 variable from the ΔQTc, ΔTAmp and ΔTpTe variables.

Among the three variables PC1, PC2 and PC3 obtained, the PC1 variable under consideration is the variable which correlates best with each of the ΔQTc, ΔTAmp and ΔTpTe. This means that the correlation coefficient that can be calculated for PC1 with each of the ΔQTc, ΔTAmp and ΔTpTe is greater (in absolute value) than the correlation coefficient that is calculated for the other principal components PC2 and PC3 for the ΔQTc, ΔTAmp or ΔTpTe in question. Table 1 of the examples clearly shows that the absolute value of the correlation coefficient of PC1 is greater than the absolute value of the correlation coefficient of PC2 and PC3, calculated for each of the ΔQTc, ΔTAmp and ΔTpTe.

If ΔTAmp was calculated according to the formula indicated above such that ΔTAmp is positive, then PC1 correlates in the same way (correlation coefficient having the same sign) with the ΔQTc, ΔTAmp and ΔTpTe. If ΔTAmp is such that it is negative, PC1 correlates in the same sense for ΔQTc and ΔTpTe, and in the other sense to ΔTAmp. Table 1 of the examples shows a PC1 that correlates negatively with ΔQTc, ΔTAmp and ΔTpTe, while PC2 correlates negatively with ΔQTc and positively with ΔTAmp and ΔTpTe. PC3 correlates negatively with ΔTAmp and positively with ΔTpTe and ΔQTc. It is also noted that the correlation coefficients of each "Δ" value are higher with PC1 than with either of the other two new variables.

The invention also relates to a method for generating an algorithm which makes it possible to generate a quantitative value associated with the appearance of an ECG feature determining an inhibition of IKr, that is to say a risk of an episode of torsade de pointes with long QT, comprising the steps mentioned above.

The invention also relates to an (in vitro or ex vivo) method for generating an algorithm which makes it possible to generate a quantitative value associated with the appearance of an ECG feature determining an inhibition of IKr, that is to say a risk of an episode of torsade de pointes with long QT, comprising the following steps:

i) obtaining the ΔQTc, ΔTAmp and ΔTpTe values corresponding to the difference, as a percentage, between the QTc, TAmp and TpTe values obtained before and after administration of a drug which prolongs QT, preferably by inhibiting the IKr channel, for each of the patients of a cohort;

ii) carrying out a principal component analysis on these ΔQTc, ΔTAmp and ΔTpTe values in order to generate three new quantitative variables PC1, PC2 and PC3.

The algorithm thus generated is the formula which makes it possible to obtain the PC1 variable from the ΔQTc, ΔTAmp and ΔTpTe variables. The PC1 value is that described above.

As seen above, the methods described can be used for determining a patient's individual risk of experiencing a ventricular repolarization disorder in the event of administration of a substance known to have a torsadogenic effect, and said composition administered to the patient is sotalol.

A method for determining a patient's individual risk of experiencing a ventricular repolarization disorder in the event of administration of a substance known to have a torsadogenic effect, characterized in that the method described above is applied to said patient, said composition administered to said patient being sotalol, according to the conditions above, is thus envisioned. The analysis of the individual risk is carried out according to the elements mentioned above.

The methods described can also be used for determining whether a substance of interest (test molecule, or test drug) has a torsadogenic nature. In this embodiment, the methods according to the invention are repeated on a cohort of patients containing a number of patients greater than or equal to 2. The various results obtained for each patient are then analyzed according to the information provided above.

As seen above, it is preferable for the method to be repeated, on each patient, with the substance of interest and at least one other composition chosen from the group consisting of a placebo and a positive control, and in particular for the positive control to be chosen from sotalol and moxifloxacin, preferably for at least one positive control to be sotalol. In this case, it is preferable to use it at a dose of 80 mg in a single intake.

The invention also relates to a device for implementing the methods described above, or a microprocessor comprising an algorithm for implementing the methods described above. In fact, the methods described above can be implemented by computer.

BRIEF DESCRIPTION OF THE FIGURES

Other features and advantages of the invention will emerge on reading the detailed description which follows, with reference to the appended figures, which illustrate.

EXAMPLES

Example 1—Generation of an Algorithm

Population/Cohort of Patients

The cohort of patients was that of the GENEREPOL study, and consisted of 995 volunteers in good health, from 18 to 60 years old, of European or North African origin. The objective of this study was to identify genetic predispositions linked to the inhibition of the IKr channel after administration of 80 mg sotalol, with a body mass index between 19 and 29 kg/m$^2$, informed consent having been received. Some other exclusion criteria were used: pregnancy, asthma, heart rate of less than 50 bpm, abnormal ECG (electrocardiogram) or QRS>100 ms, systolic blood pressure<100 mmHg, history of atrioventricular block or Raynaud's phenomenon, known chronic disease such as heart or kidney failure requiring chronic treatment, QT-prolonging drug or any chronic treatment, except contraceptive pills, analgesics and vitamins, family or personal history of congenital long QT syndrome, of arrhythmia, sudden death, or QTc (Fridericia method, QTcF)>450 ms.

Protocol for Measuring the ECG

The volunteers were hospitalized at 8 a.m. for a period of approximately 6 hours after having had no food intake overnight.

An intravenous catheter was inserted for taking blood samples. The ECG of the patients was then recorded using the Cardioplug device (Cardionics Inc®, Brussels, Belgium) connected to a laptop computer. The basal ECG recordings (each carried out in triplicate, for 10 seconds) were obtained after the patients had been resting on their back for 10 minutes. A single oral dose of 80 mg of sotalol was then given to the patients and the ECG monitoring was continued. Three hours after sotalol had been taken (H10), the ECG was again recorded (in triplicate) after the subjects had remained lying on their back for 10 minutes and before lunch.

At H3, a blood sample was taken in order to determine the plasma sotalol concentration. The participants were released 5 to 6 hours after having taken sotalol, after having verified that the QTcF was below the basal QTcF+40 ms.

Analysis of the ECGs

Insofar as the increase in QT by sotalol represents the equivalent of the congenital iatrogenic form of long QT syndrome, LQT2, the appearance of the conventional differences between the basal trace and the trace three hours after taking sotalol was verified on the ECG.

The QTcF, TpTe and TAmp and the presence of notches (double peak) in the T wave were quantified. Fridericia's correction (QTcF) was used to correct the QT with respect to the heart rate, in accordance with the ICH guidelines E14.

The ECG data analysis was carried out with the CARDIABASE software (Groupe Banook, Nancy, France).

The quantitative analysis of the QTcF, TpTe and TAmp was carried out by two trained investigators, in order to limit the inter-evaluator variability.

TpTe was measured by the tangent method, in triplicate, on a representative beat (average representation of an ECG of 10 seconds) on the V3, V4 and V5 leads. In the event of a double peak of the T wave (notch), the peak taken into consideration was the first peak, if though the amplitude of the T wave was smaller for this peak. The average value obtained was retained. In the event of it being impossible to measure TpTe on V3, V4 or V5, the measurement was instead carried out on V2 (for V3), or V6 (for V4N5).

In order to measure TAmp, positioning was on the site of the maximum amplitude of the first peak of the T wave on a representative beat (average representation of an ECG of 10 seconds) on the DII, V2 and V3 leads. The average of the TAmp values resulting from these three leads, and measured on three different ECGs of 10 seconds (in triplicate), was calculated and retained. If it was not possible to measure a TAmp on one of these leads (in particular because of a low value (<0.1 mV)), the V4 lead was used.

QTcF was measured by the tangent method on the DII lead for three consecutive beats and the average value of an evaluation in triplicate was retained.

It was possible to verify that the measurements remained consistent and reproducible between the evaluators.

For these parameters, the difference between the value obtained at H3 and the basal value was measured. This difference was expressed as percentage relative to the basal value, and the calculations were carried out such that the value calculated is positive.

The following calculations were therefore carried out:

$$\Delta QTcF\ (\%) = (QTcF\ at\ H3 - QTcF\ basal)/(QTcF\ basal) \times 100$$

$$\Delta TpTe\ (\%) = (TpTe\ at\ H3 - TpTe\ basal)/(TpTe\ basal) \times 100$$

$$\Delta TAmp\ (\%) = (TAmp\ basal - TAmp\ \partial H3)/(TAmp\ basal) \times 100$$

In order to evaluate the double peaks (notches), all the ECGs were evaluated independently by two investigators. The patients were described as notchers or non-notchers, in the event of agreement between the two investigators. In the event of disagreement in the evaluation, the subjects were not included in these groups (only 10 subjects in the evaluation cohort and 8 subjects in the replication cohort could thus be not classified).

Principal Component Analysis

A principal component analysis was carried out on the calculated values ΔQTcF, ΔTpTe and ΔTAmp, which made it possible to generate three non-correlated alternative markers, taking better account of the information carried by the three initial correlated values. The statistical analyses were carried out with the R software (https://www.r-project.org/).

Results
Sotalol-Induced Changes in the Electrocardiogram

The changes observed in the electrocardiogram three hours after administration of sotalol suggest an inhibition of the IKr channel, with results and observations similar in the exploration and replication cohorts, regardless of the qualitative or quantitative parameters evaluated.

In agreement with previous studies, sotalol also induces absolute and relative changes in the duration of QTcF (21.4±14 ms and 5.5±3.5% respectively).

Typical changes in the shape of the T wave were also observed, with an increase in TpTe (14.2±15.6 vs 15.9±20.5%, p=ns (not significant)) and a decrease in TAmp (13.6±15.7 vs 12.8±15.3%, p=ns) respectively between the exploration and replication cohorts.

However, a large inter-subject variability was observed in all the changes observed. The variations in TpTe, TAmp and QTcF between H3 and the basal level exhibit an autocorrelation in the same proportion between the two cohorts.

Finally, 40 (8%) or 51 (10%) subjects exhibited a double peak (notch) in the two cohorts. They were almost exclusively women, and these patients had a higher ΔTpTe, ΔQTcF and ΔTAmp than those observed for the non-notchers (patients without double peak (notch)).

Principal Component Analysis

The principal component analysis made it possible to generate three new quantitative values, linked to the sotalol-induced modifications of ventricular repolarization.

The first component (PC1) explaining approximately 65-67% of the phenotypic variance reflects the typical modifications after inhibition of the IKr channel, that is to say the increase in TpTe and QTcF and the decrease in TAmp (table 1).

A significant decrease in the PC1 value ($p<10^{-4}$) was observed in the patients exhibiting a double peak (notchers) compared with the patients not exhibiting this double peak (non-notchers) in one or other of the exploration (−2.5±1.5 vs 0.3±1.1) or replication (−2.3±1.8 vs 0.3±1.1) cohorts.

Figure 1:
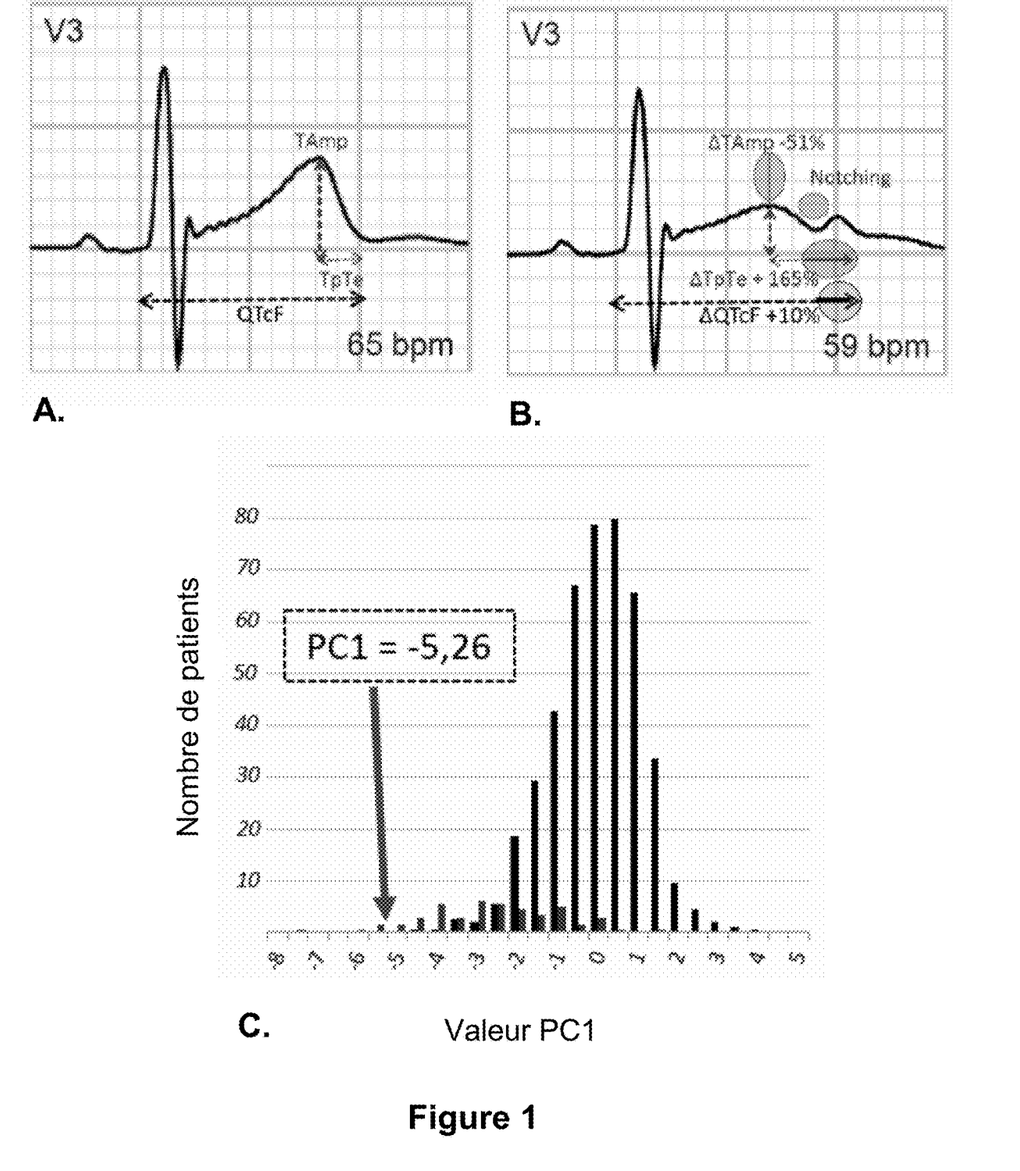
FIG. 1 shows a representative electrocardiogram trace, in a patient, before (1.A) and three hours after taking sotalol (1.B), and also the PC1 value obtained for this patient, represented relative to the distribution of the PC1 values in the population (1.C). The double peak of the T wave (notch) is observed, and the fact that the PC1 value is among the furthest away from 0.
Figure 2:
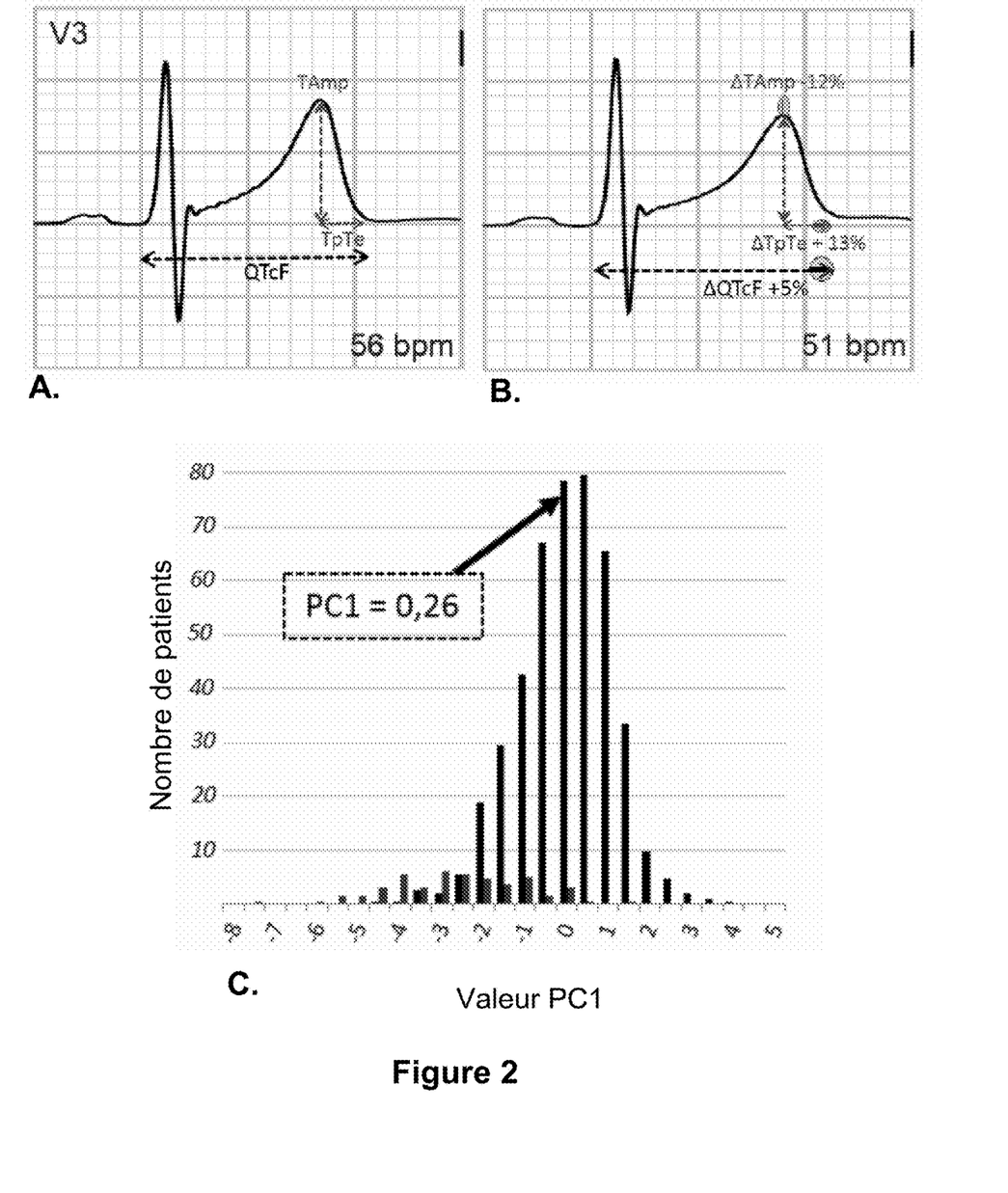
FIG. 2 shows a representative electrocardiogram trace, in another patient, before (1.A) and three hours after taking sotalol (1.B), and also the PC1 value obtained for this other patient, represented relative to the distribution of the PC1 values in the population (1.C). This patient shows a weak sotalol-induced IKr inhibition. The PC1 value calculated is therefore close to 0.

The PC1 value is therefore a quantitative alternative value of the inhibition of IKr. The distribution of the PC1 values is shown in FIGS. 1 and 2 with the example of a patient exhibiting an extreme IKr inhibition, with double peak (notch), and an extreme negative PC1 value (FIG. 1), and a patient exhibiting a weak IKr inhibition (FIG. 2).

The other principal components (PC2 and PC3) explained, respectively, approximately 19-21% and 14% of the phenotypic variance.

TABLE 1

Correlations (r) between ΔTAmp, ΔTpTe, ΔQTcF and the principal components in the exploration cohort (n = 489, upper part of the table) or the replication cohort (n = 495, lower part of the table).

| Correlation (r) | ΔTAmp | ΔTpTe | ΔQTcF | PC1 | PC2 | PC3 |
| --- | --- | --- | --- | --- | --- | --- |
| ΔTAmp | 1 | 0.59 | 0.40 | −0.83 | 0.36 | −0.43 |
| ΔTpTe | 0.58 | 1 | 0.45 | −0.85 | 0.23 | 0.47 |
| ΔQTcF | 0.47 | 0.46 | 1 | −0.73 | −0.68 | −0.06 |
| PC1 | −0.84 | −0.84 | −0.78 | 1 | 0 | 0 |
| PC2 | 0.28 | 0.3 | −.063 | 0 | 1 | 0 |
| PC3 | −0.46 | 0.45 | 0.01 | 0 | 0 | 1 |

It is clearly observed that PC1 correlates in the same sense with ΔTAmp, ΔTpTe, and ΔQTcF (correlated negatively in this example), which is not the case for PC2 or PC3.

It is also observed that the absolute value of the correlation coefficients of PC1 with ΔTAmp, ΔTpTe and ΔQTcF is greater than that of PC2 or PC3 with these values.

CONCLUSION

As expected, an increase in TpTe and QTcF and a decrease in TAmp were observed between the basal level and three hours after taking sotalol.

The new PC1 value obtained by principal component analysis of ΔQTcF, ΔTpTe and ΔTAmp explains most of the total variance of the "Δ" data (ΔQTcF, ΔTpTe and ΔTAmp) and is thus associated with the common mechanism of increase in QTcF and TpTe, associated with the decrease in TAmp, and is a quantitative and integrative marker for drug-induced IKr inhibition.

Example 2—Application of the Algorithm for Identifying a Drug Interaction with an Increased Risk of IKr Inhibition Population The study was carried out on 615 women in good health, of European or North African type, between the ages of 18 and 60, with a QTcF<450 ms, and no known disease or chronic, or chronic treatment, except for contraception, and without any family history of congenital long QT syndrome, arrhythmia, or sudden death.

Measurement and Calculation of the Various QTcF, TAmp and TpTe Data

The QTcF, TAmp and TpTe were measured according to the same protocol as for example 1, before and three hours after administration of a single oral dose of sotalol at 80 mg.

The ΔQTcF, ΔTpTe and ΔTAmp were also calculated.

Principal Component Analysis

A principal component analysis was carried out on the ΔQTcF, ΔTpTe and ΔTAmp (XLStat software, Addinsoft®) in order to generate three new decorrelated values.

Results

The PC1 variable, which correlates in the same way with ΔQTcF, ΔTpTe and ΔTAmp (that is to say which correlates the most and in the same sense with each of these variables), explains 63% of the phenotypic variance observed (characterized by the increase in QTcF and TpTe and the decrease in TAmp).

It is also observed that the absolute value of PC1 is significantly greater for women taking drospirenone as contraception, compared with the group of women with no contraception (respectively 0.56 [−0.13; 1.5] and 0.09 [−0.58; 1.1], p<0.05). In this example, PC1 resulting from the analysis of a subgroup exclusively of women correlates positively with ΔQTcF (r=0.71), ΔTpTe (r=0.85) and ΔTAmp (r=0.83) and the more positive values of PC1 are linked to a greater inhibition of IKr.

Likewise, the women taking drospirenone had more double peaks (notches) three hours after taking sotalol (25.8%) than the women not taking an oral contraceptive (13.4%).

No difference was observed with regard to the plasma sotalol concentration in these two groups.

These results are consistent with the pharmacological properties of drospirenone, which has a lower androgenic potential than other pills, the protective nature of testosterone being known.

GENERAL CONCLUSION

Example 1 clearly shows that the application of an algorithm makes it possible to determine a patient's individual response to sotalol, and the sensitivity of this patient to drug-induced inhibition of the IKr channel (and therefore to the risk of torsade de pointes).

Example 2 clearly shows that the method described herein (use of an algorithm based on the principal component analysis of ΔQTcF, ΔTpTe and ΔTAmp) makes it possible to identify, for a given substance (in this case drospirenone), the QT-prolongation-inducing and IKr-channel-inhibiting nature.

The invention claimed is:

1. An ex vivo method for generating an algorithm which makes it possible to generate a quantitative value associated with the appearance of an ECG feature determining an inhibition of IKr comprising the following steps:
   i) obtaining the ΔQTc, ΔTAmp and ΔTpTe values corresponding to the difference, as a percentage or absolute value, between the QTc, TAmp and TpTe values obtained before and after administration of a drug which prolongs QT by inhibiting the IKr channel for each patient of a cohort, with
      (1) QTc=QT interval corrected with respect to the heart rate;
      (2) TAmp=maximum amplitude of the first peak of the T wave; and
      (3) TpTe=interval between the maximum first peak of the T wave and the end of the T wave;
   ii) carrying out a principal component analysis on these ΔQTc, ΔTAmp and ΔTpTe values in order to generate three new quantitative variables PC1, PC2 and PC3, said algorithm being the formula which makes it possible to obtain the PC1 variable from the ΔQTc, ΔTAmp and ΔTpTe, the variable PC1 being the variable which correlates most with each of ΔQTc, ΔTAmp and ΔTpTe.

2. The method as claimed in claim 1, wherein the cohort contains a number of patients greater than or equal to 50.

3. The method as claimed in claim 1, wherein TAmp was measured on the D2, V2, V3 leads.

4. The method as claimed in claim 1, wherein TpTe was measured on the V2, V3, V4 leads.

5. The method as claimed in claim 1, wherein QTcF was measured on the D2 leads.

6. The method as claimed in claim 1, wherein at least one value TAmp, TpTe or QTcF was measured on an averaged complex.

7. An ex vivo method for determining the risk of induction of a torsadogenic effect after administration of a composition to a patient, comprising the following steps:
   I. combining the ΔQTc, ΔTAmp and ΔTpTe values corresponding to the difference, as a percentage or absolute value, between the QTc, TAmp and TpTe values obtained before and after administration of said composition, in an algorithm, obtained by the method as claimed in claim 1;
   II. obtaining a final result of this combination; and
   III. comparing the value of this final result to a reference value.

8. The method as claimed in claim 7, wherein the final result obtained in step II is obtained by application of the algorithm: a1×ΔTAmp (%)+a2×ΔQTcF (%)+a3×ΔTpTe (%)+b, with $-0.05 \leq a1 \leq -0.03$; $-0.2 \leq a2 \leq -0.1$; $-0.04 \leq a3 \leq -0.02$; $1.5 \leq b \leq 2$.

9. The method as claimed in claim 7, wherein the final result obtained in step II is obtained by application of the algorithm: a1×ΔTAmp (%)+a2×ΔQTcF (%)+a3×ΔTpTe (%)+b, with $a1=-0.038 \pm 0.002$; $a2=-0.15 \pm 0.001$; $a3=-0.031 \pm 0.002$; $b=1.79 \pm 0.05$.

10. The method as claimed in claim 7, wherein it is used for determining a patient's individual risk of experiencing a ventricular repolarization disorder in the event of administration of a substance known to have a torsadogenic effect, and that said composition administered to the patient is sotalol.

11. The method as claimed in claim 7, wherein said composition is a substance of interest and that said method is used for determining whether the substance of interest has, as such, a torsadogenic nature, said method being repeated on a cohort of patients containing a number of patients greater than or equal to 2.

12. The method as claimed in claim 11, wherein the method is repeated, on each patient, with the substance of interest and at least one other composition chosen from the group consisting of a placebo and a positive control.

13. The method as claimed in claim 12, wherein the positive control is chosen from sotalol and moxifloxacin.

14. The method as claimed in claim 13, wherein the positive control is sotalol, used at 80 mg in a single intake, and that said substance of interest has a more torsadogenic nature than sotalol if the average of the final results obtained for the patients of the cohort after administration of the substance of interest is less than the average of the final results obtained for the patients of the cohort after administration of sotalol.

15. The method as claimed in claim 7, wherein TAmp was measured on the D2, V2, V3 leads.

16. The method as claimed in claim 7, wherein TpTe was measured on the V2, V3, V4 leads.

17. The method as claimed in claim 7, wherein QTcF was measured on the D2 lead.

18. The method as claimed in claim 7, wherein at least one TAmp, TpTe or QTcF value was measured on an averaged complex.

* * * * *